United States Patent [19]

Utsugi

[11] 4,452,236
[45] Jun. 5, 1984

[54] ENDOSCOPE WITH A RESILIENT RAISING MEMBER

[75] Inventor: Mikio Utsugi, Tokyo, Japan

[73] Assignee: Olympus Optical Co., Ltd., Tokyo, Japan

[21] Appl. No.: 375,990

[22] Filed: May 7, 1982

[30] Foreign Application Priority Data

May 14, 1981 [JP] Japan ................................ 56-72739

[51] Int. Cl.³ .............................................. A61B 1/00
[52] U.S. Cl. ...................................................... 128/4
[58] Field of Search ........................................ 128/4-8

[56] References Cited

U.S. PATENT DOCUMENTS 3,561,432  2/1971  Yamaki .................... 128/6
3,896,793  7/1975  Mitsui et al. ............. 128/6
3,924,608  12/1975  Mitsui ..................... 128/6
4,190,041  2/1980  Chikama .................. 128/4

Primary Examiner—Edward M. Coven
Assistant Examiner—Max F. Hindenburg

[57] ABSTRACT

An elastic raising member is disposed in a raising member housing provided at the distal end of an insertion section of an endoscope and has one end of which is supported by the housing and the other end of which is a free end. When the free end is pulled by a control wire extending along the insertion section by operating a control unit, the raising member changes the guiding direction of a treatment tool. When the free end is released, the raising member is restored to a lying position by its elasticity.

8 Claims, 10 Drawing Figures

ENDOSCOPE WITH A RESILIENT RAISING MEMBER

BACKGROUND OF THE INVENTION

The present invention relates to an endoscope having a treatment tool guide section.

A conventional endoscope has a channel for inserting and guiding a treatment tool such as a forceps therethrough. A guide unit for guiding the tool is disposed at the opening of the channel. Referring to FIG. 1, this unit has a raising lever housing 2 in a distal end assembly 1 of the endoscope. A raising lever 3 is pivotal about a shaft 4 in the raising lever housing 2, as shown in FIG. 1. A control wire 5 connected to the raising lever 3 is pulled or pushed to change a raising angle of the raising lever 3. Thus, a treatment tool 6 is arbitrarily oriented at a desired angle.

In the conventional device of this type, the raising lever 3 is pivoted by strongly pulling the control wire 5. The raising lever 3 returns to the lying position by pushing the control wire 3. However, the force applied to the direction to push the control wire 5 is hard to be transmitted, preventing smooth pushing of the control wire 5. Especially, when contamination causes clogging at the shaft 4 or a wire insertion hole 7, the raising level 3 may not return to the lying position. Further, since the raising lever 3 has a predetermined shape and is not flexible, a portion 6a which is sharply bent is formed when a raising angle is increased. The treatment tool 6 is often broken at the portion 6a. The raising lever becomes thick and the distal end portion becomes large in the conventional endoscope.

SUMMARY OF THE INVENTION

It is, therefore, an object of the present invention to provide an endoscope which is capable of properly returning a raising member to a non-pulling position when the raising member is not pulled by a control wire, which is capable of preventing sharp bending of a treatment tool and smoothly guiding the treatment tool even if a raising angle is increased, and which has a small distal end portion having the raising member therein.

In order to achieve the above object of the present invention, there is provided an endoscope comprising: an elongated insertion section which has a distal end portion to be inserted into a body cavity with a raising member housing open to the outside, a proximal end portion to be located outside the body cavity, a longitudinal axis extending from said proximal end portion to said distal end portion, and a treatment tool insertion channel extending from said proximal end portion to said distal end portion along said axis and communicating with said raising member housing; a control section connected to said proximal end portion of said insertion section and having a treatment tool insertion inlet port which communicates with said treatment tool insertion channel; an elastic raising member having an acting portion and a supported portion and adapted to change a guiding direction of the treatment tool as the acting portion pushes the intermediate portion of the tool and raises the same to a desired position, said supported portion being supported by part of said distal end assembly, said acting portion being movable between raised and laid positions and so that said raising member by itself is resiliently returned to the laid position after it is raised; a control wire one end of which is connected to said acting portion of said raising member, the other end of which reaches said control section, and which is inserted in said insertion section along said axis; and a traction control unit, provided in said control section and connected to said control wire, for raising said raising member to change the guiding direction of the treatment tool.

DETAILED DESCRIPTION OF THE PREFERRED EMBODIMENTS

Figure 1:
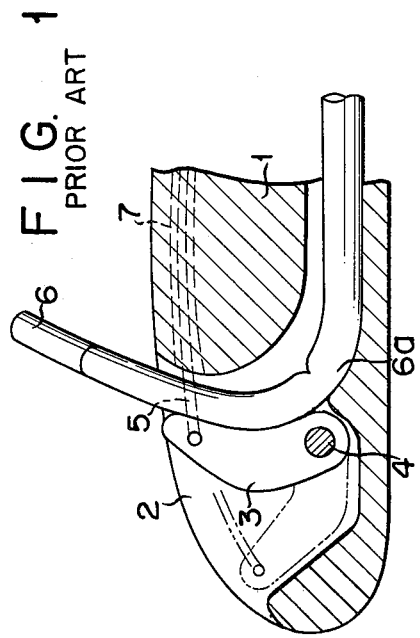
FIG. 1 is a side sectional view of a treatment tool guide unit used in a conventional endoscope.
Figure 2:
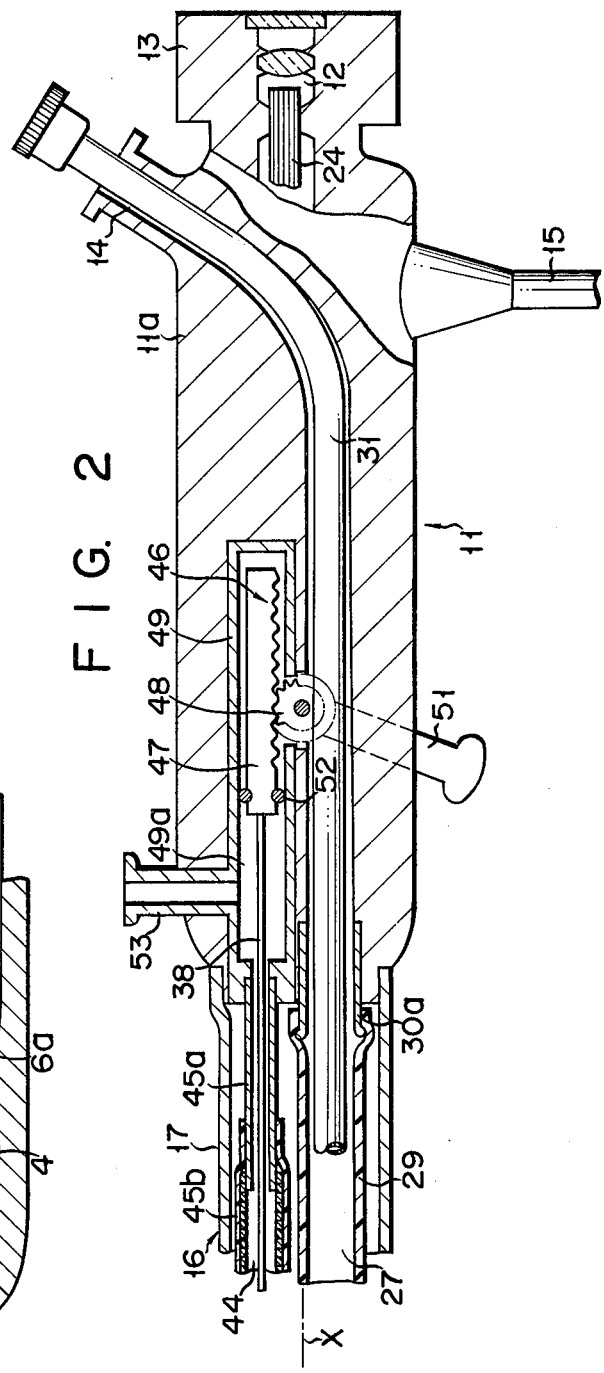
FIG. 2 is a side sectional view of a control section of an endoscope and a portion in the vicinity of a proximal end portion of an insertion section of the endoscope according to one embodiment of the present invention.
Figure 3:
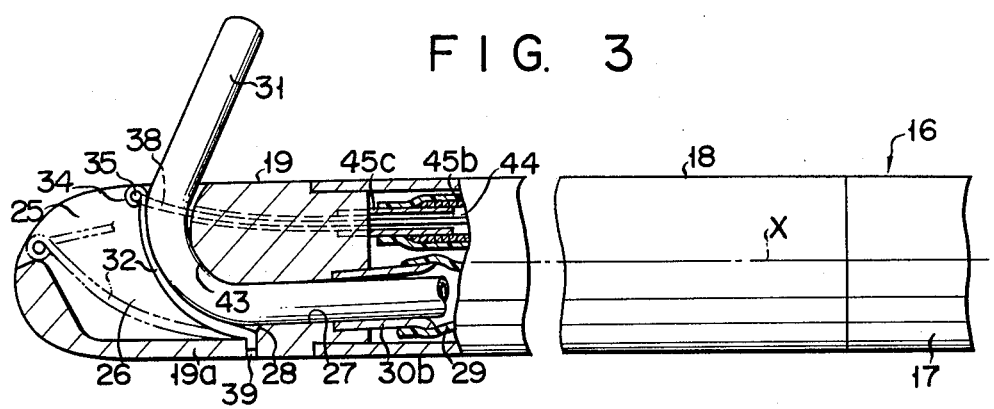
FIG. 3 is a side sectional view of a portion in the vicinity of a distal end portion of the insertion section of the endoscope shown in FIG. 2.
Figure 4:
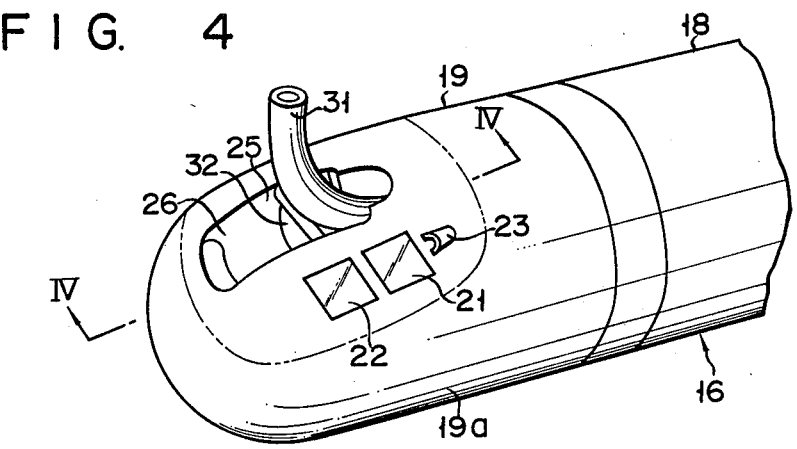
FIG. 4 is a perspective view of the distal end portion of the endoscope shown in FIG. 2.

Referring to FIG. 2, a control section 11 of an endoscope has a control section main body 11a. The control section main body 11a has an eyepiece section 13 having an eyepiece optical system 12 and a treatment tool insertion inlet port 14. One end of a universal cord 15 is connected to the control section main body 11a. The other end of the universal cord 15 has a connector (not shown) which is connected to a light source unit (not shown). A proximal end portion of an elongated insertion section 16 is connected to the control section main body 11a. The insertion section 16 comprises a flexible tube 17, a bending tube 18 and a distal end assembly 19. The bending tube 18 is disposed between the distal end of the flexible tube 17 and the proximal end of the distal end assembly 19. The bending tube 18 is remote-controlled by a control knob (not shown) which is disposed in the control section 11. The distal end assembly 19 and part of the insertion section 16 near the distal end assembly 19 constitute a distal end portion of the insertion section 16 to be inserted in a body cavity. In the above embodiment, the parts of the bending tube 18 and the flexible tube 17 which are on the distal end portion are inserted in the body cavity. A proximal end portion of the flexible tube 17 which is positioned outside the body cavity during examination constitutes a proximal end portion. As shown in FIGS. 2 and 3, a longitudinal axis X of the insertion section 16 extends from the proximal end portion to the distal end portion. An observation window 21, an illumination window 22 and an air/water supply nozzle 23 oriented toward the outer surface of the observation window 21 are disposed on one side surface of the distal end assembly 19, as shown in FIG. 4. The distal end of an image guide 24 (FIG. 2) using optical fibers is optically connected to the observation window 21. The image guide 24 is inserted in the insertion section 16 along the axis X thereof. The proximal end of the image guide 24 extends into the control section 11 and is optically connected to the eyepiece optical system 12. Further, the distal end of a light guide (not shown) using optical fibers is optically connected to the illumination window 22. The proximal end of the light guide is connected to the connector of the universal cord 15 through the insertion section 16, the control section main body 11a, and the universal cord 15. When the connector is connected to a light source unit, this light guide is optically connected to a light source (not shown) of the light source unit. Thus, the illumination window receives illumination light. The illumination light transmitted through the light guide emerges from the illumination window 22 toward the field of sight in the body cavity.

As shown in FIG. 3, a raising member housing 26 having a guide port 25 open to the field of the sight of the observation window 21 is formed at a main body 19a of the distal end assembly 19. The raising member housing 26 communicates with a treatment tool outlet port 28 of the treatment tool insertion channel 27.

The channel 27 extends through the flexible tube 17, the bending tube 18 and the distal end assembly 19 along the axis X of the insertion section 16 and communicates with the treatment tool insertion port 14 of the control section 11. Part of the channel 27 which extends in the flexible tube 17 and the bending tube 18 is formed by a flexible tube 29 and connecting tubes 30a and 30b. A treatment tool 31 is inserted from the treatment tool insertion port 14 and is guided into the channel 27. The channel 27 then guides the treatment tool 31 to the raising member housing 26. The treatment tool 31 varies in accordance with a specific therapy. Typical examples of the treatment tools are a forceps and a tube for a contrast agent. The tube for a contrast agent is illustrated in the figure.

Figure 6:
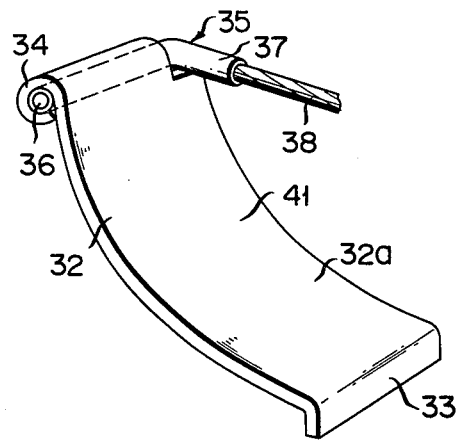
FIG. 6 is a perspective view of a raising member of the endoscope shown in FIG. 2.

A raising member 32 is disposed in the raising member housing 26 to change the direction of the treatment tool 31 extending from the guide port 25. The raising member 32 is oriented from the outlet port 28 of the channel 27 to the guide port 25. The raising member 32 is formed by an elongate plate comprising an ultraelastic member such as an elastic alloy. As shown in FIG. 6, one edge 33 of the raising member 32 is bent perpendicularly and the other edge is curled in the same direction of one edge 33 to form a fulcrum portion 34. One end 36 of an L-shaped rigid pin 35 is rotatably fitted in the fulcrum portion 34. An end of a metal control wire 38 is connected to the other end 37 of the raising member 32. Part of the pin 35 is notched and the other end 37 of the pin 35 is located at the notched part of the raising member 32. The other end 37 of the pin 35 is mounted with a sufficient space within the width of the raising member 32. One edge 33 of the raising member 32 is fitted in a groove 39 formed on the bottom wall of the raising member housing 26 in the vicinity of the outlet port 28 of the channel 27. The edge 33 of the raising member 32 defines a supported portion. Thus, the edge 33 of the raising member 32 is inserted in the groove 39 at part of the housing 26 and is supported thereby. The other edge of the raising member 32 is constituted as a free end 41. An acting portion comprising a smooth surface of the free end 41 is disposed perpendicularly to the outlet port 28 of the channel 27.

Figure 10:
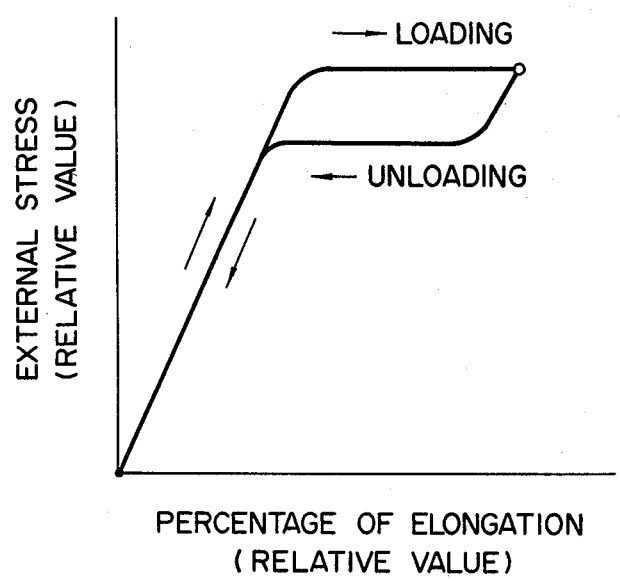
FIG. 10 is a graph for explaining the elongation of an ultraelastic alloy as a function of an external stress.

As described above, the raising member 32 comprises a plate-shaped elastic material. However, when it is pulled by the controlled wire 38, the raising member 32 is bent upwards and takes a raised position as indicated by the solid line in FIG. 3. When it is not pulled, the raising member 32 is slightly bent and lies in a laid position as indicated by the alternate long and two dashed line in FIG. 3. A stainless steel plate of 0.03 to 0.5 mm thickness is generally used as the material of the raising member 32. An ultraelastic alloy is preferred. The ultraelastic alloy has such an ultraelasticity as will be described below. It is often called "pseudo-elasticity alloy". A Ti-Ni type alloy is one of the ultraelastic alloys. When a load is increasingly applied to a material, yielding occurs after linear elastic deformation. In other words, apparent plastic deformation occurs. When the load is eliminated from the material, distortion is also eliminated. As a result, the metal of this type can be repeatedly used as a spring in a range wider than other metal materials (FIG. 10). The apparent plastic deformation described above occurs by the martensite transformation by the stress. The distortion is eliminated by the reverse transformation when the load is eliminated from the metal. The distortion range within which the metal may be repeatedly used as the spring varies in accordance with a ratio of constituents of the metal. A metal having an elongation percentage of about 6% can be used.

A pair of stoppers 42 located on the side of the outlet port 28 of the channel 27 are formed in the raising member housing 26. When the raising member 32 is bent, the pair of stoppers 42 gradually comes in contact with both side edges 32a of the regulating surface of the raising member 32 from its one end to the other end so that the raising member 32 is positioned at a desired position. Further, when the raising member 32 is bent at maximum, the regulating surface of the raising member 32 is completely in tight contact with the stoppers 42. Thus, the pair of stoppers 42 has substantially an arcuated shape to bend the treatment tool 32 optimally.

Figure 5:
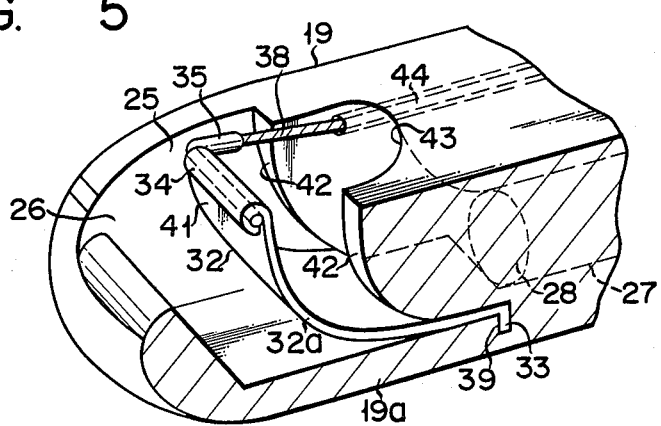
FIG. 5 is a perspective view of the distal end portion which is partially cut along the line IV—IV in FIG. 4.

As shown in FIG. 5, a U-shaped groove 43 is formed in the end wall of the raising member housing 26 at the side of the channel 27 and between the pair of stoppers 42. The center of the groove 43 is substantially arcuated along the surfaces of the pair of stoppers 42.

The depth of the groove 43 from the upper surfaces of the stoppers 42 substantially corresponds to the inner diameter of the treatment tool outlet port 28. Therefore, when the raising member 32 is bent at maximum and is in tight contact with the stoppers 42, a treatment tool path having the same width as that of the treatment tool outlet port 28 is formed between the raising member 32 and the groove 43.

The control wire 38 is connected to the projecting end of the free end 41 of the raising member 32 through the pin 35. Since the pin 35 which comprises a highly rigid material is bent in an L shape, the side to which the control wire 38 is connected may not be bent more than the other side when the control wire 38 is pulled strongly. Both sides of the raising member 32 are thus uniformly bent.

The other end of the control wire 38 is guided to the control section 11 through a wire insertion hole 44. The wire insertion hole 44 is formed by wire guide tubes 45a, 45b and 45c.

The other end of the control wire 38 is connected to a traction control unit 46 disposed in the control section 11. The traction control unit 46 comprises a rack 47 disposed in the control section main body 11a and a pinion gear 48 meshed therewith. The control wire 38 is connected to the rack 47.

The rack 47 is movably mounted in a cylinder 49. When the pinion gear 48 is rotated by a control lever 51 disposed outside of the control section 11, the position of the rack 47 is controlled along the axis X of the insertion section 16.

A packing 52 is mounted at the outer periphery of the rack 47 on the side of the control wire 38 to liquid-tightly seal a cylinder chamber 49a of the cylinder 49 from the side of the wire insertion hole 44. A cleaning liquid inlet port 53 is formed in the cylinder chamber 49a so that the cleaning liquid inlet port 53 communicates with the cylinder 49. A gap is formed between the wire insertion hole 44 and the control wire 38 to allow flow of the cleaning liquid.

The mode of the operation of the endoscope according to the first embodiment of the present invention will be described.

The treatment tool 31 is inserted from the treatment tool inlet port 14. When the treatment tool 31 is guided through the treatment tool outlet port 28, the user should not pull the control wire 38. In the condition in which the raising member 32 lies as shown in the alternate long and two dashed line in FIG. 3, the user must push the treatment tool 31 into the treatment tool insertion channel 27. The distal end of the treatment tool 31 slides on the surface of the acting portion of the raising member of the raising member housing 26 and projects into the body cavity through the delivery port 25. When the distal end of the treatment tool 31 comes in the field of sight for the observation window 21, the user controls the traction control unit 46 to pull the control wire 38. The free end 41 of the raising member 32 is bent and raised. Then, the treatment tool 31 is bent and oriented toward a desired direction. Thus, with a change in an angle of the raising member 32, the user controls to position the treatment tool 31 at a desired angle.

If the user wishes to bend the treatment tool 31 at maximum, he pulls the control wire 38 strongly so that the both side edges 32a of the raising member 32 are brought into tight contact with the stoppers 42. Therefore, the raising member 32 is bent with a proper curvature along the arcuated surface of the stoppers 42. The treatment tool path having substantially the same width as the treatment tool outlet port 28 is formed between the raising member 32 and the groove 43. Even if the raising member is bent at maximum, the treatment tool 31 is smoothly inserted along the raising member 32 and part of the treatment tool 31 may not be sharply bent, preventing damage of the treatment tool 31.

If the user wishes to release bending of the treatment tool 31, he releases traction force by the traction control unit 46. The control wire 38 is naturally loosened. Subsequently, the raising member 32 returns to the position by its elasticity, as indicated by the alternate long and two dashed line in FIG. 3. The treatment tool 31 restores its original shape by itself.

The cleaning liquid is supplied to the cylinder chamber 49a through the cleaning liquid inlet port 53. Further, the cleaning liquid is supplied to the raising member housing 26 through the wire insertion hole 44. Contamination causing clogging in the wire insertion hole 44 or the like is washed off, allowing smooth movement of the control wire 38. If a disinfection liquid is used in place of the cleaning liquid, the wire insertion hole 44 and the control wire 38 can be disinfected.

In the above embodiment, since the elastic member is used as the raising member 32, the control wire need not be pushed strongly to restore the original shape. The control wire is only loosened or may be slightly pushed by the weak force to automatically restore the raising member 32 to the lying position easily.

Even when the control wire 38 is not pulled, the raising member 32 is properly restored to the original position, improving the operability of the endoscope. Further, since the control wire 38 need not be pushed, the control wire 38 may be smaller to assure a wider gap between the control wire 38 and the wire insertion hole 44. Therefore, the cleaning liquid flows smoothly, increasing the cleaning efficiency.

Further, since a rotary member such as a shaft is not used for the raising member 32 and the raising member 32 is fixed at the distal end assembly 19, movement of the raising member 32 may not be prevented by deposition of contamination and is moved smoothly.

Further, since the raising member 32 is thinner, it can be stored in a small raising member housing 26. Therefore, the outer diameter and the axial length of the distal end assembly 19 are decreased, resulting in a compact distal end assembly 19. As opposed to the conventional complicated raising member manufactured by milling, the raising member 32 does not require complex procedure, resulting in low cost and easy manufacture.

Further, when the ultraelastic alloy is used as the material of the raising member 32, plastic deformation does not occur within the elongation range of, for example 6%. Thus, the treatment tool 31 is properly bent with a small curvature. This metal can maintain its elasticity over a long period of time. For example, a Ti-Ni type alloy as the ultraelastic alloy has an excellent resistance to a cleaning/disinfection liquid and to acids such as gastric juice. Further, this alloy is nontoxic to the human body.

The control wire 38 is not limited to a metal one. For example, a solid wire or strand may be used.

Figure 7:
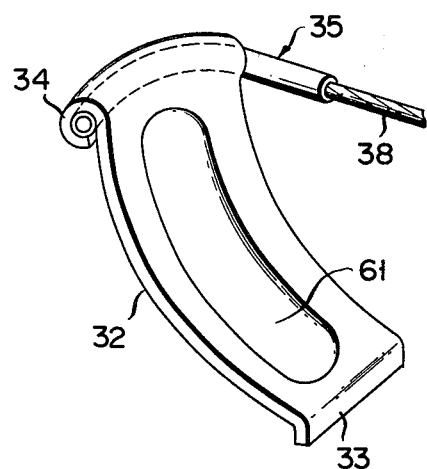
FIGS. 7 to 9 are perspective views of raising members according to second to fourth embodiments of the present invention, respectively.

FIG. 7 shows a raising member of the endoscope according to a second embodiment of the present invention. The material and the like of the raising member in the second embodiment are substantially the same as those in the first embodiment except that a groove 61 is formed to guide the treatment tool smoothly on the surface which extends from one end to the other end (insertion direction of the treatment tool) and which opposes the treatment tool outlet port 28 of the channel 27. The treatment tool 31 is guided on the groove 61, so that the treatment tool 31 does not deviate from the predetermined route nor swing in a direction perpendicular to the groove 61. Thus, guiding operation is further improved.

Figure 8:
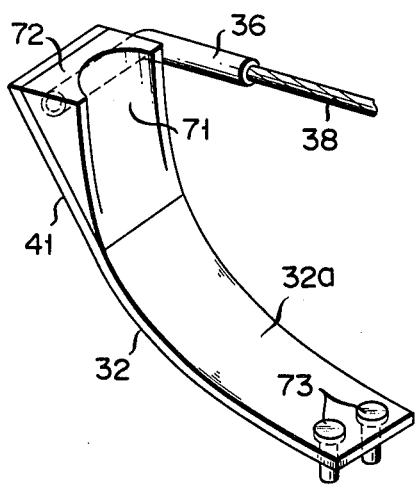

FIG. 8 shows a raising member of the endoscope according to a third embodiment of the present invention. The raising member 32 has a guide member 72 with a recess 71 formed on the free end 41 of an elastic plate member 32a to guide the treatment tool. This guide member 72 which comprises a metal or synthetic resin also has the same function as the groove 61. A means for fixing the supported portion of the raising member 32 to the distal end assembly 19a may be rivets 73, screws or caulkings, as shown in FIG. 8.

Figure 9:
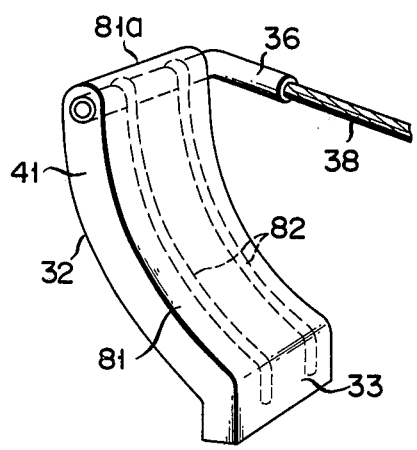

FIG. 9 shows a raising member of the endoscope according to a fourth embodiment of the present invention. Elastic metal wires 82 are embedded in a raising member main body 81 made of a soft and flexible synthetic resin. The metal wires 82 extend from one edge 33 of the main body 81 to the other edge 81a of the main body 81. A fluorine type synthetic resin or the like which has a low friction coefficient may be used as the material of the raising member main body 81 to guide the treatment tool smoother.

In order to use the raising members shown in FIGS. 7 to 9 in the same manner as that shown in FIG. 5, a notched portion (not shown) for positioning the control wire 38 of the pin 35 freely is formed in the stoppers 42. The control wire 38 is preferably guided through the notched portion. With the above arrangement, when the raising member 32 is raised at maximum, the pin 35 is fitted in the notched portion and does not interfere with the raising operation.

Since the raising member 32 need only have elasticity, it may not be formed by a metal. A synthetic resin such as a nylon, a polycarbonate, a hard rubber may also be used to form a single member which is formed in the same shape as shown in FIGS. 6 to 9.

The thickness of the raising member 32 may not be uniform over the entire length. For example, the thickness of the raising member 32 may be changed so as to obtain an accurately arcuated shape.

According to the present invention, the control wire need not be pushed to cause the raising member to restore the original lying shape. The control wire is only released for this purpose. Further, in accordance with traction of the control wire, the raising member is bent so that part of the treatment tool may not be sharply bent, resulting in smooth insertion of the treatment tool. The raising member may be made of a plate having a small thickness as needed. Therefore, the raising member can be stored in a small raising member housing, resulting in a compact distal end assembly.

What is claimed is:

1. An endoscope comprising: an elongated insertion section which has a distal end portion to be inserted into a body cavity with a raising member housing open to the outside, a proximal end portion to be located outside the body cavity, a longitudinal axis extending from said proximal end portion to said distal end portion, and a treatment tool insertion channel extending from said proximal end portion to said distal end portion along said axis and communicating with said raising member housing; a control section connected to said proximal end portion of said insertion section and having a treatment tool insertion inlet port which communicates with said treatment tool insertion channel; a resilient raising member which includes an elastic plate positioned in said raising member housing and having an acting portion and a supported portion and adapted to change a guiding direction of a treatment tool as the acting portion pushes an intermediate portion of the tool and raises the same to a desired position, said supported portion being supported by part of said distal end portion of the elongated insertion section, said acting portion being movable between raised and lowered positions so that said raising member by itself is resiliently returned to the lowered position after being raised; a control wire, one end of which is connected to said acting portion of said raising member, the other end of which reaches said control section, and which is inserted in said insertion section along said axis; and a traction control unit, provided in said control section and connected to said control wire, for raising said raising member to change the guiding direction of the treatment tool.

2. An endoscope according to claim 1, wherein said raising member is made of an ultraelastic alloy.

3. An endoscope according to claim 2, wherein said ultraelastic alloy is a Ti-Ni type alloy.

4. An endoscope according to claim 1, wherein said acting portion of said raising member has a groove formed therein to guide the treatment tool along the insertion direction of the treatment tool.

5. An endoscope according to claim 1, wherein said elastic plate constitutes the supported portion and a rigid member attached to the elastic plate constitutes the acting portion of said raising member.

6. An endoscope according to claim 1, wherein a stopper is formed in said raising member housing and comes in contact with said raising member to define the guiding direction of the treatment tool when said raising member is raised to the raised position.

7. An endoscope according to claim 1, wherein said raising member is made of an elastic synthetic resin plate.

8. An endoscope comprising: an elongated insertion section which has a distal end portion to be inserted into a body cavity with a raising member housing open to the outside, a proximal end portion to be located outside the body cavity, a longitudinal axis extending from said proximal end portion to said distal end portion, and a treatment tool insertion channel extending from said proximal end portion to said distal end portion along said axis and communicating with said raising member housing; a control section connected to said proximal end portion of said insertion section and having a treatment tool insertion inlet port which communicates with said treatment tool insertion channel; a resilient raising member positioned in said raising member housing and having an acting portion and a supported portion and adapted to change a guiding direction of a treatment tool as the acting portion pushes an intermediate portion of the tool and raises the same to a desired position, said raising member including a main body made of a flexible synthetic resin and an elongate elastic metal member embedded in said main body and extending to the acting portion from the supported portion, said supported portion being supported by part of said distal end portion of the elongated insertion section, said acting portion being movable between raised and lowered positions so that said raising member by itself is resiliently returned to the lowered position after being raised; a control wire, one end of which is connected to said acting portion of said raising member, the other end of which reaches said control section, and a traction control unit, provided in said control section and connected to said control wire, for raising said raising member to change the guiding direction of the treatment tool.

* * * * *